United States Patent
Thompson et al.

(10) Patent No.: US 7,548,059 B2
(45) Date of Patent: Jun. 16, 2009

(54) PIPELINE INSPECTION TOOL WITH SPIRALLY ARRANGED SENSOR BLOCKS

(75) Inventors: Ronald J. Thompson, Maple (CA); Thomas Cook, Burlington (CA); George Kucherenko, Mississauga (CA); Paul Holloway, Sherwood Park (CA)

(73) Assignee: Intratech Inline Inspection Services Ltd., Mississauga, Ontario (CA)

( * ) Notice: Subject to any disclaimer, the term of this patent is extended or adjusted under 35 U.S.C. 154(b) by 393 days.

(21) Appl. No.: 11/238,686

(22) Filed: Sep. 29, 2005

(65) Prior Publication Data

US 2006/0220640 A1    Oct. 5, 2006

Related U.S. Application Data

(60) Provisional application No. 60/667,061, filed on Apr. 1, 2005.

(51) Int. Cl.
*G01N 27/72* (2006.01)
*G01R 33/12* (2006.01)

(52) U.S. Cl. ...................... 324/220; 73/865.8

(58) Field of Classification Search ............... 324/219, 324/220, 221; 73/865.8, 866.5, 592, 622, 73/623

See application file for complete search history.

(56) References Cited

U.S. PATENT DOCUMENTS 3,786,684 A * 1/1974 Wiers et al. ............. 73/866.5
5,454,276 A 10/1995 Wernicke
5,614,825 A 3/1997 Maxfield et al.
6,100,684 A 8/2000 Ramaut
6,762,602 B1 7/2004 Laursen et al.
2003/0136195 A1 7/2003 Krieg et al.
2003/0183022 A1 10/2003 Sapelnikov et al.

FOREIGN PATENT DOCUMENTS

WO    WO 97/12237    4/1997

* cited by examiner

*Primary Examiner*—Patrick J Assouad
*Assistant Examiner*—David M. Schindler
(74) *Attorney, Agent, or Firm*—Dykema Gossett PLLC (57) ABSTRACT

A pipeline inspection tool has a spirally arranged series of blocks, with each block having a magnet and at least one magnetic flux sensor. An axially extending support may be provided which terminates in mounts and the series of blocks may be mounted between the mounts. The support may be arranged so as to permit bending of said series of blocks but resist torsion of said series of blocks. A supporting tendon may extend from a second of the mounts through a first opening in each block around a tendon supporting pulley of the first of the mounts and back through a second opening in each block to the second mount. A compression spring surrounding each arm of the tendon between the tendon support and the series of blocks. The magnet of each block may be arranged such that a like pole of each magnet is at one side of the series of blocks. The poles of each magnet may be longitudinally elongated and the longitudinally elongated poles may be directed along an axis of said tool. The magnetic flux sensors of each block may be between the poles of the magnet of each block.

19 Claims, 9 Drawing Sheets

PIPELINE INSPECTION TOOL WITH SPIRALLY ARRANGED SENSOR BLOCKS

CROSS-REFERENCE TO RELATED APPLICATION

This application claims priority from U.S. provisional patent application No. 60/667,061 filed Apr. 1, 2005.

BACKGROUND

Underground pipelines are commonly used to carry oil, natural gas and other fluids. If a leak develops in the pipeline, at best this will result in the loss of some of the fluid being transported. More likely, however, the leak may present an increasing environmental hazard, and the leak may become more severe with time. Further, more catastrophically, a pipeline may rupture. A rupture, particularly of a natural gas pipeline, can cause an explosion and fire. Obviously, it is therefore preferable to identify the location of a potential leak or rupture so that the compromised portion of the pipeline may be repaired or replaced. A variety of pipeline inspection tools exist for this purpose, some of which inspect the pipeline as they pass through it. A tool that passes through the pipeline to inspect it is often referred to in the industry as a pig. A pig may have magnets which create flux lines along the axis of the pipe. Disturbances in the flux density as the tool moves through the pipe can then be interpreted to determine if these disturbances are indicative of a compromised section of pipeline.

A drawback with a tool that creates axial flux lines is that it will not detect axially directed cracks or flaws. To address this drawback, some tools employ one or more additional magnets, each additional magnet providing transversely directed flux lines. However, this modified tool suffers the drawback that the flux sensors between the poles of each of these additional magnets are each exposed to different flux densities, which reduces the accuracy of the measurements.

Therefore, there is a need for an improved pipeline inspection tool.

SUMMARY OF THE INVENTION

A pipeline inspection tool has a spirally arranged series of blocks, with each block having a magnet and at least one magnetic flux sensor.

An axially extending support may be provided which terminates in mounts and the series of blocks may be mounted between the mounts. The support may be arranged so as to permit bending of said series of blocks but resist torsion of said series of blocks. A supporting tendon may extend through an opening in each block of the series of blocks and be mounted to the mounts of the support. Urging means, such as a compression spring, may act between a first one of the mounts and the series of blocks for resiliently compressing the blocks together. The compression spring may extend around the tendon. The opening in each block may be a first opening and the tendon may extend from a second one of the mounts, through each first opening, around a tendon support of a first of the mounts and back through a second opening in each block to the second mount. The tendon support may be a pulley which allows movement of the tendon, and there may be a compression spring surrounding each arm of the tendon between the tendon support and the series of blocks. The second one of the mounts may be resilient. A head-end block having a first opening and a second opening may receive the tendon and have a magnet but no magnetic flux sensor. The head-end block may be positioned between the compression spring surrounding each arm of the tendon and the series of blocks. Similarly, a tail-end block having a first opening and a second opening may receive the tendon and have a magnet but no magnetic flux sensor. The tail-end block may be positioned between the second mount and the series of blocks.

The magnet of each block may be arranged such that a like pole of each magnet is at one side of the series of blocks. The poles of each magnet may be longitudinally elongated and the longitudinally elongated poles may be directed along an axis of said tool. The magnetic flux sensors of each block may be between the poles of the magnet of each block.

The series of blocks may be one of a plurality of series of blocks, each block of each of the plurality of series of blocks will then have a magnet and at least one magnetic flux sensor and, for a given series of blocks, the magnet of said each block may be arranged such that a like pole of each magnet is at one side of the given series of blocks, the plurality of series of blocks being disposed side-by-side. There may be an even number of plurality of series of blocks and the plurality of series of blocks may be equally angularly spaced about a circumference of said tool. A block at one end of the first spirally arranged series of blocks may be angularly displaced from a block at an opposite end of said first spirally arranged series of blocks by an angle equaling about the quotient of 360° over the number of series of blocks. A given pole of each block of said given series of blocks may be adjacent a like pole of a circumferentially adjacent series of blocks such that the plurality of series of blocks repel one another. There may be four series of blocks and a block at one end of said first spirally arranged series of blocks is angularly displaced from a block at an opposite end of said spirally arranged series of blocks by about ninety degrees.

In another aspect, a pipeline inspection tool has a serially arranged series of blocks, each block having an energy generator and at least one energy sensor; an axially extending support terminating in mounts, the series of blocks being mounted between the mounts of the support; a tendon extending from a second one of said mounts, through a first opening in said each block, around a tendon support of a first of the mounts, the tendon support allowing movement of said tendon, and back through a second opening in said each block to the second mount.

Other features and advantages will become apparent from the following description in conjunction with the drawings.

BRIEF DESCRIPTION OF THE DRAWINGS

In the figures which illustrate an example embodiment of the invention.

DETAILED DESCRIPTION

Figure 1:
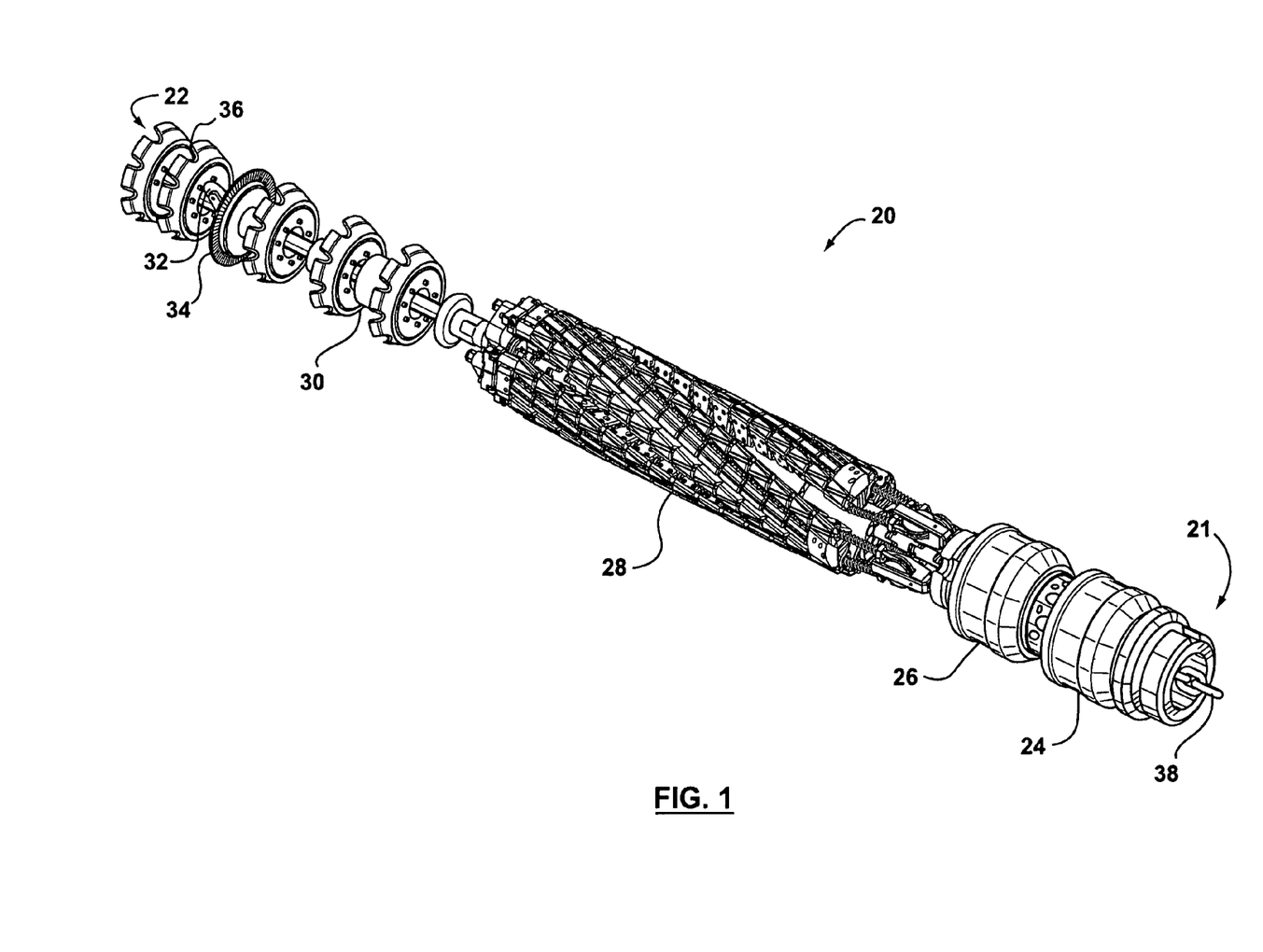
FIG. 1 is a perspective view of a pipeline inspection tool made in accordance with this invention.

With reference to FIG. 1, a pipeline inspection tool 20, which is often referred to as a pig in the industry, may comprise, from nose 21 to tail 22: cups 24, a transmitter 26, a flux generating and detecting unit 28, an electronics unit 30, an odometer 32, an internal corrosion detection unit 34, and a battery unit 36. The cups may be fabricated of a flexible polymer and sized to make an interference fit with the walls of the pipe to be inspected. The pig may be inserted into the pipe with its nose 21 downstream of its tail 22. In consequence of this, the fluid pressure in the pipe acts against the open ends of the cups 24 to force the tool to travel along the pipeline. The nose 21 may further be provided with a loop 38 so that, as an alternative, the pig 20 may be tethered to a line and pulled through the pipeline.

Transmitter 26 may be used to transmit a location signal from the pig. As will be further explained hereinafter, the flux generating and detecting unit 28 may generate magnetic flux in the pipe and detect flux densities. The electronics unit 30 may receive flux density data from the flux generating and detecting unit 28 and store this data. Odometer 32 may measure the distance the pig has travelled and output distance data to electronics unit 28 for storage. Internal corrosion detection unit 34 may detect internal corrosion of on the pipeline (but not its severity) and also send this to the electronics unit for storage. And battery unit 36 may provide power for powering the active components of the pig.

All but the flux generating and detecting unit 28 of the pig are conventional components in other pigs and are believed to be understood by those skilled in the art. Hence, these components are not further detailed herein.

Figure 2:
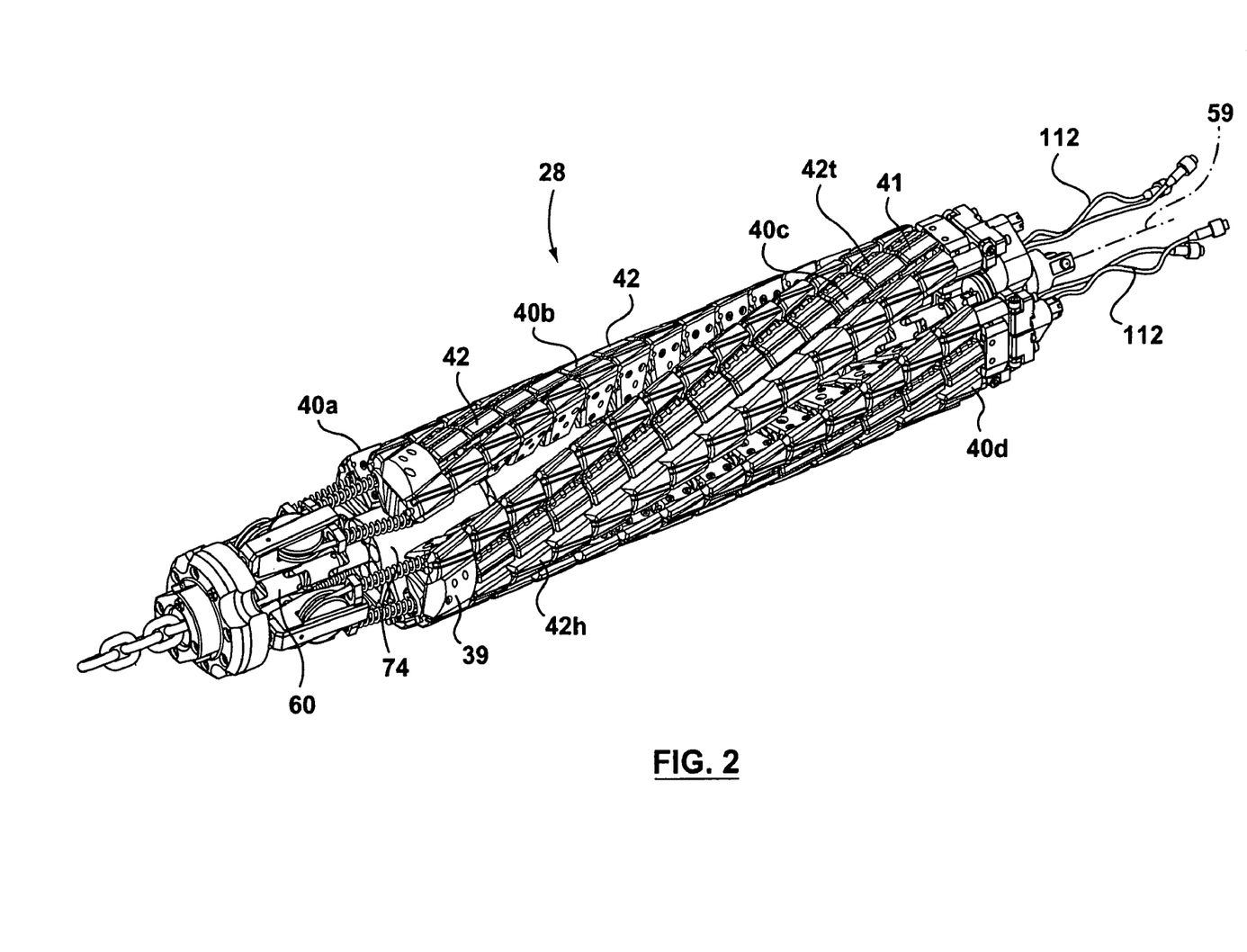
FIG. 2 is an enlarged perspective view of a portion of FIG. 1.
Figure 3:
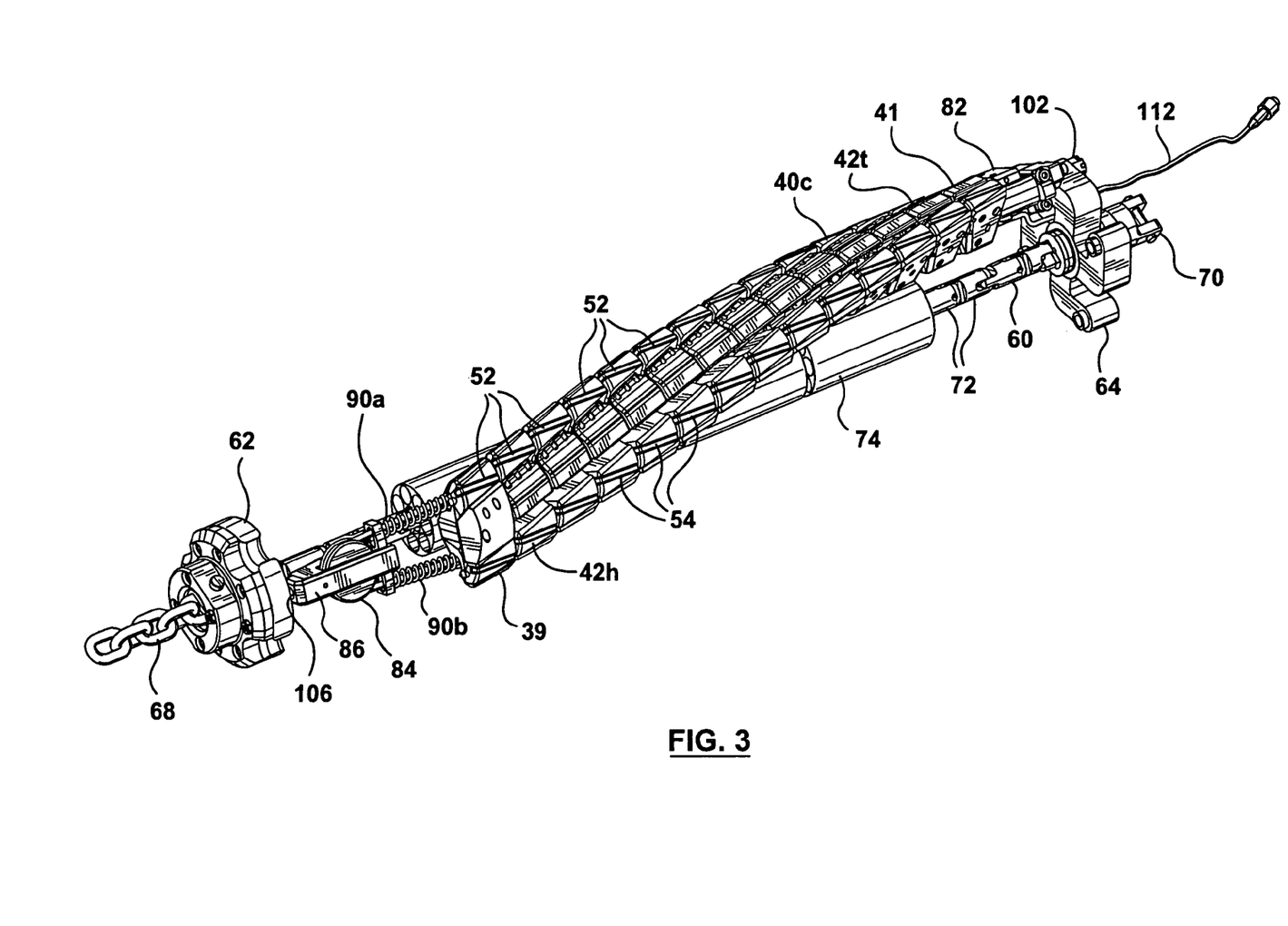
FIG. 3 is a perspective view of a portion of FIG. 2.

Turning to FIGS. 2 and 3, the flux generating and detecting unit 28 may have four skids 40a, 40b, 40c, and 40d equally spaced about the circumference of the unit 28. Each of these four skids may have fourteen serially arranged blocks: head end conditioning block 39, twelve identical sensing blocks 42, and tail end conditioning block 41. Each skid may be spirally arranged, with a sensing block 42h at the head end of blocks 42 of a given skid circumferentially displaced by about ninety degrees from a sensing block 42t at the tail end of blocks 42 of that same skid.

Figure 4:
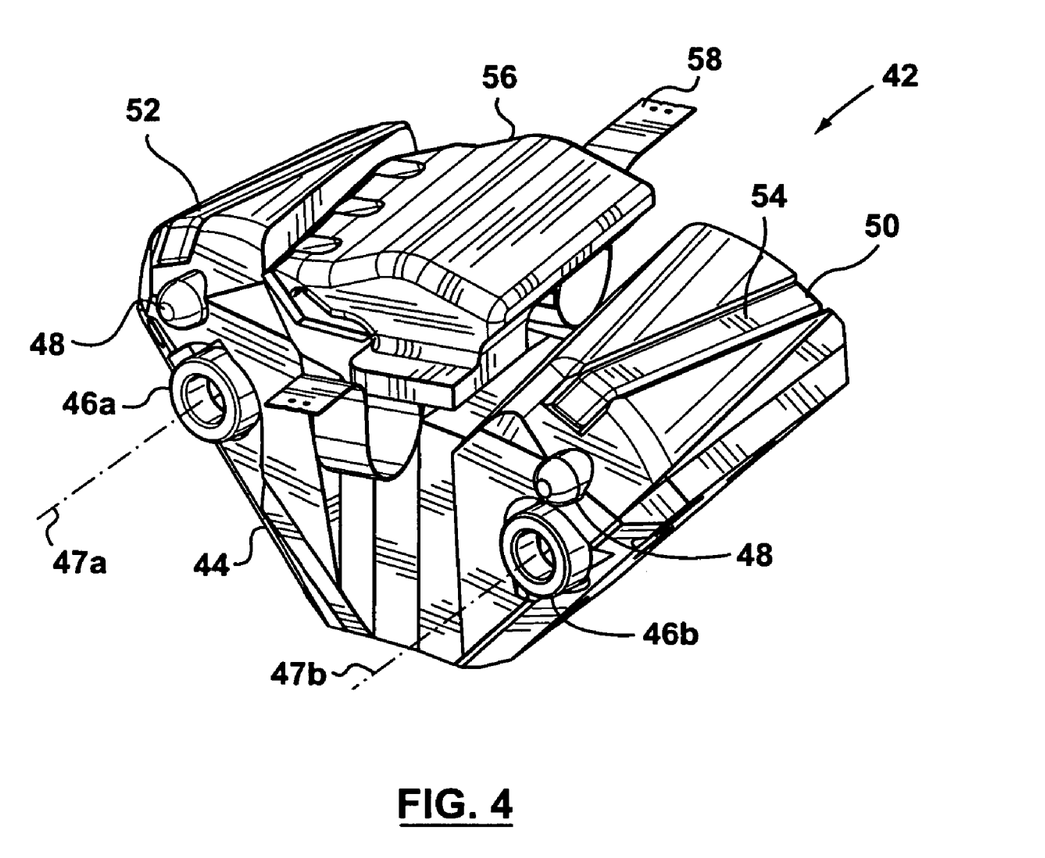
FIG. 4 is an enlarged perspective view of another portion of FIG. 1, FIGS. 5a and 5b are perspective views of a portion of FIG. 4.

Turning to FIG. 4, a sensing block 42 has a base 44 with a pair of through bores 46a, 46b with parallel bore axes 47a, 47b, respectively, and head and tail end bumpers 48 (only the head end bumpers being visible in FIG. 4). The base 44 envelops a generally V-shaped magnet 50 such that the opposed poles 52, 54 of the magnet protrude from the top of the base. The magnet 50 may be a permanent magnet or, although not preferred due to power constraints, an electromagnet. As will be apparent, the poles 52, 54 are generally rectangularly shaped, and these rectangularly shaped poles extend parallel to each other. Further, the rectangularly shaped poles are directed at an angle to the parallel axes 47a, 47b of the bores 46a, 46b and this angle may be about 7.5°. The base 44 supports a flux density sensing unit 56 between the magnetic poles 52, 54. An electrical bus 58 is electrically connected to the sensing unit.

It will be apparent from FIGS. 2 and 3 that, due to the angle chosen between the rectangular-shaped magnetic poles and the through bores 46a, 46b (FIG. 4) in the blocks 42, the rectangular-shaped magnetic poles generally parallel the central axis 59 of the unit 28.

Figure 5A:
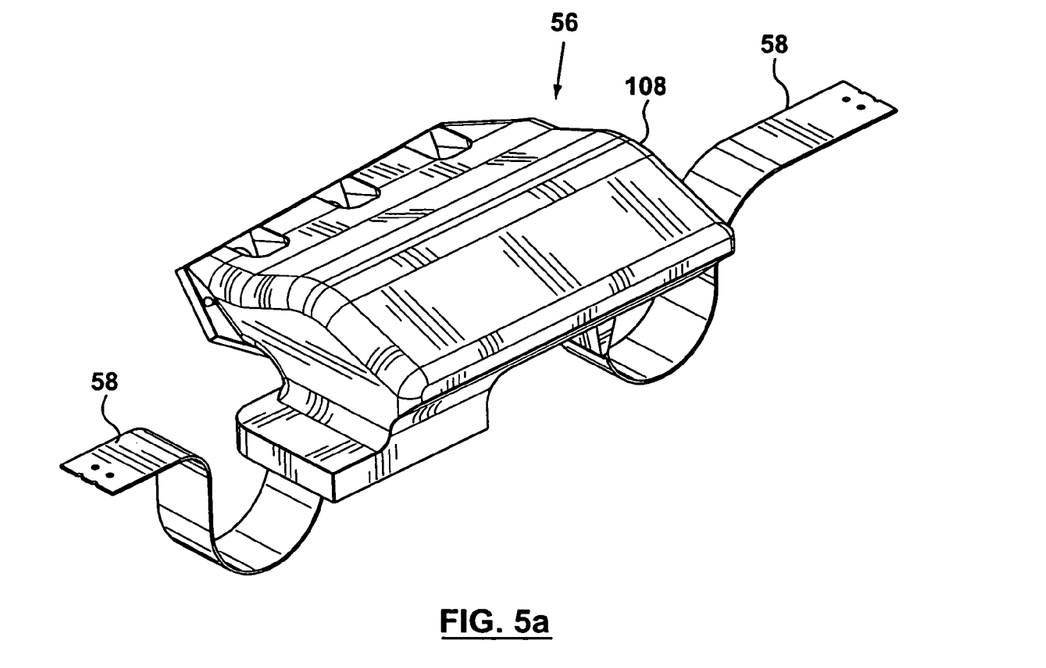
Figure 5B:
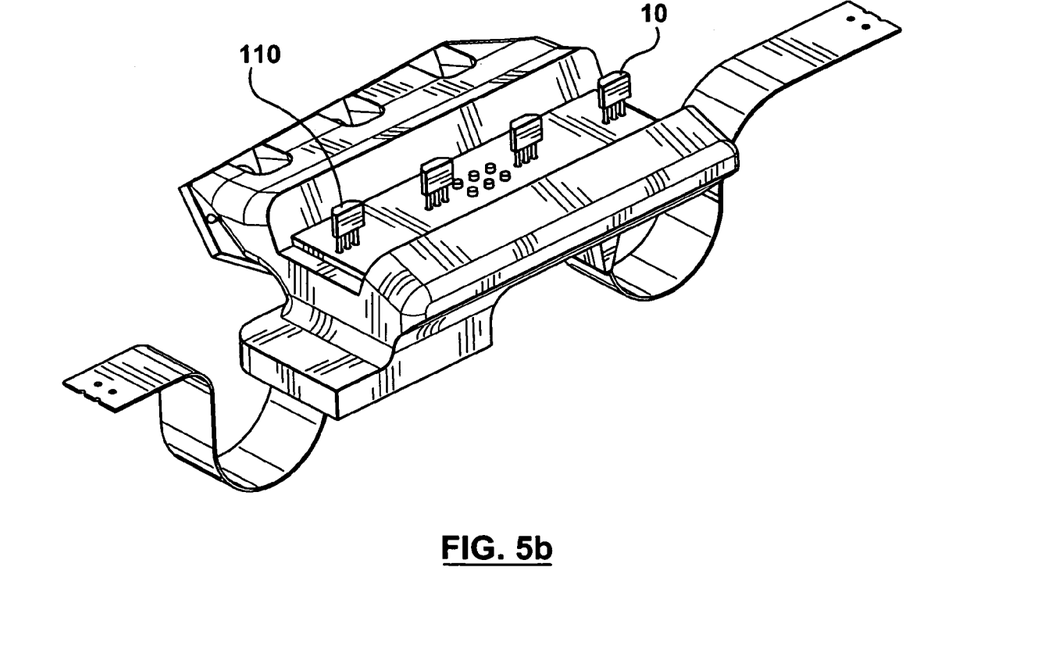

Turning to FIGS. 5a and 5b, a sensing unit 56 may have a cover 108 protecting a plurality of magnetic flux sensors 110. These sensors 110 may be Hall effect sensors and they are arranged in a line parallel to the rectangularly shaped poles 52, 54 of magnet 50. The sensors may be operatively connected to bus 58 so that the flux densities sensed by the sensors are output to the bus 58. Bus 58 connects the sensors of adjacent sensing blocks 42 (FIG. 2) so that the flux densities sensed by each of the sensors of each of the blocks of a skid are output to bus 58. The bus 58 associated with each of the four skids terminates at its tail end in data line 112 (FIG. 2). Each of the four data lines may be connected to the electronics unit 30 (FIG. 1) so that the electronics unit receives and stores the flux density data.

Figure 6:
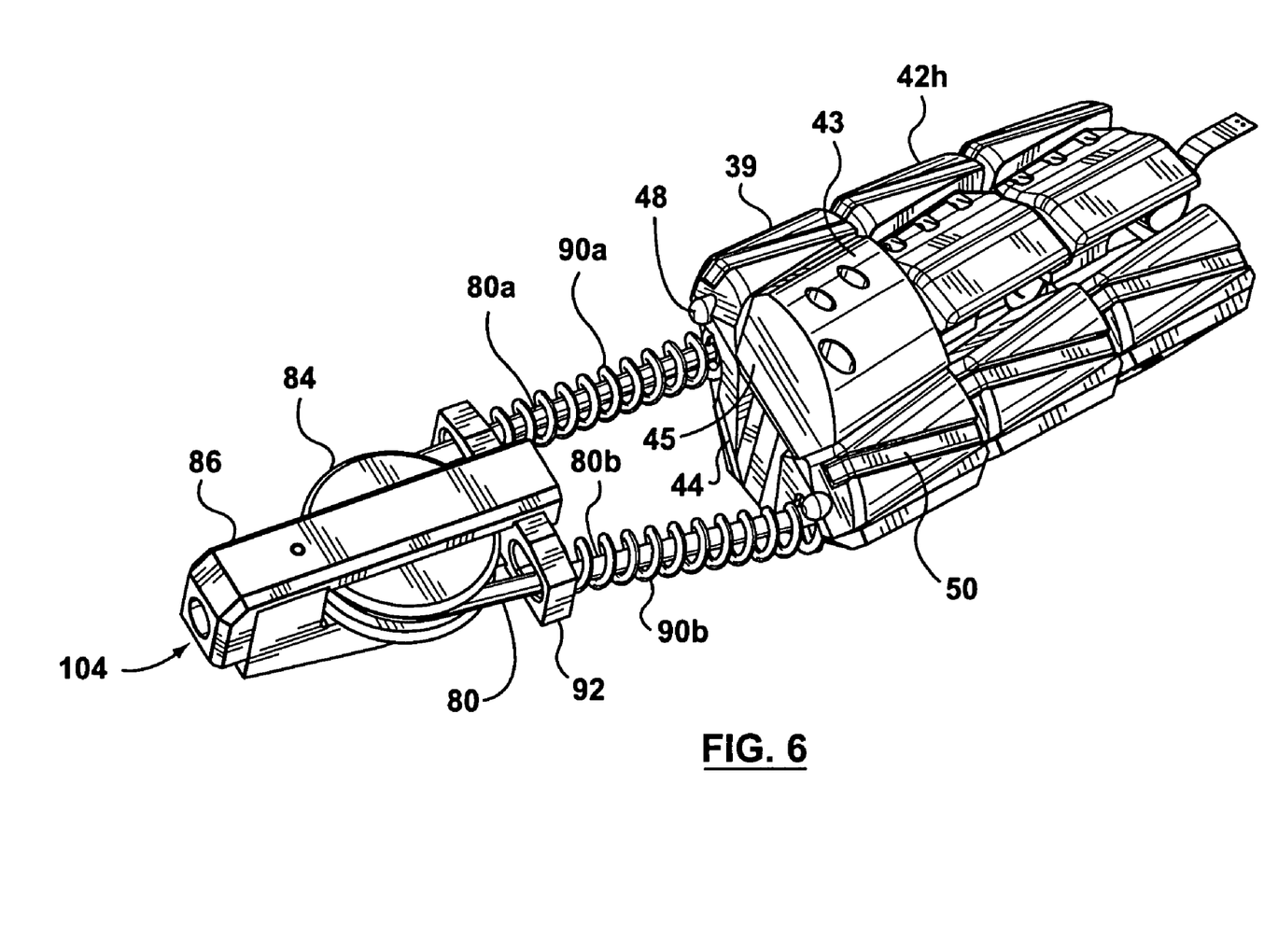
FIG. 6 is an enlarged perspective view of another portion of FIG. 1.

Referring to FIG. 6, the head end conditioning block 39 in a skid may have an enlarged and hardened dome 43 with a forward face 45 which is bevelled. Further, the head end conditioning block 39 and tail end conditioning block 41 (FIG. 3) have a base 44 (with a magnet 50) identical to that of base 44 of sensing blocks 42. On the other hand, the conditioning blocks 39, 41 have no magnetic flux sensors.

Returning to FIGS. 2 and 3, unit 28 may have an articulated central dowel 60 extending between a nose piece 62 and a tail piece 64. The nose piece may have a connector 68 to connect to the transmitter 26 (FIG. 1) and the tail piece may have a connector 70 to connect to the electronics unit 30 (FIG. 1). The tail piece may be fabricated of a resilient material, such as a polymer material. The articulated dowell may be comprised of a series of cylindrical stubs 72 each pinned to the next to allow a single degree of bending freedom and with adjacent stubs having pins at ninety degrees to one another so as to provide for universal bending of the dowell but resist torsional forces. The dowel 60 may be enveloped by a series of resilient annular cylinders 74, which provide a resilient backstop for the skids 40, 40b, 40c, 40d. The cylinders may be fabricated of a polymeric material, such as polyurethane.

Figure 7:
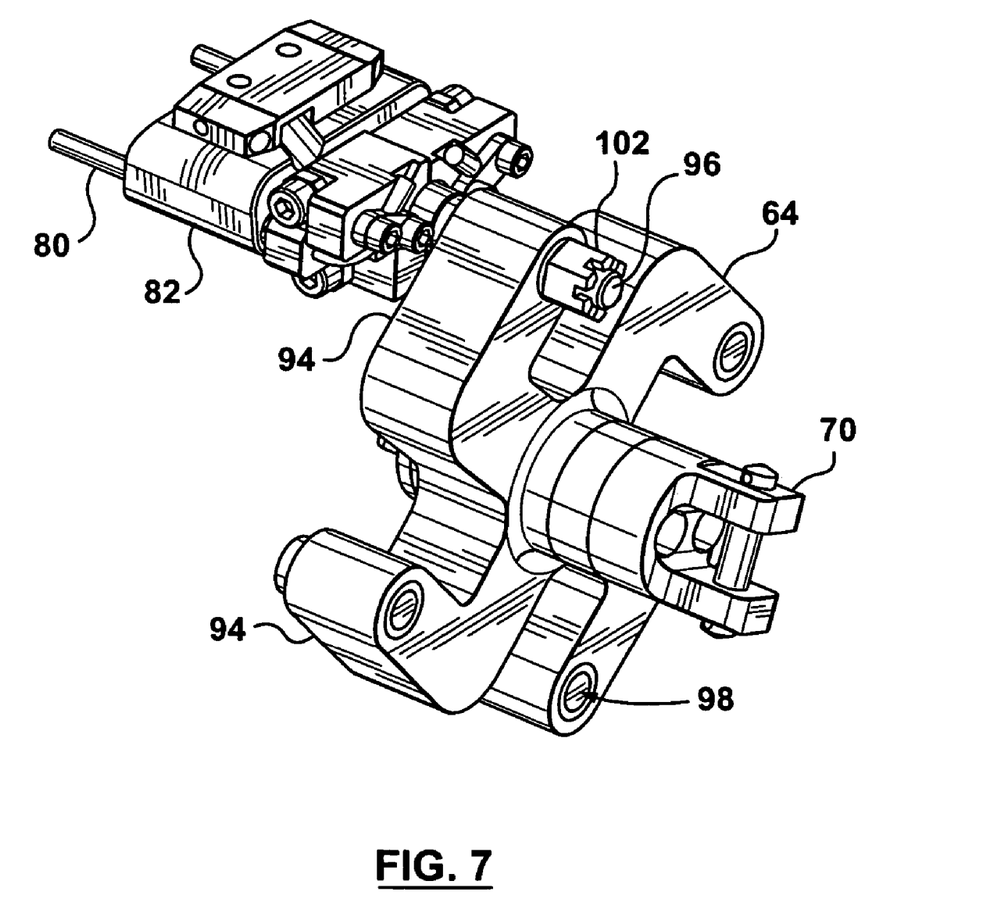
FIG. 7 is an enlarged perspective view of another portion of FIG. 1.

With reference to FIGS. 6 and 7 along with FIGS. 2 and 3, for each skid, a tendon 80 may extend from a mount 82 attached to tail piece 64, through the first through bore 46a in the base 44 of each block 39, 41, 42 of the skid, around a pulley 84 supported by a frame 86 mounted to nose piece 62, and back through the second through bore 46b in the base 44 of each block 39, 41, 42 to mount 82. Compression springs 90a, 90b may surround each arm 80a, 80b of the looped back tether 80 and be compressed between the head end conditioning block 39 and a spring backstop 92 of the pulley frame 86. The springs 90a, 90b act to compress the blocks 39, 41, 42 of a skid together. The blocks of a skid abut at their bumpers 48.

Tail piece 64 may have a "swastika" shape with each of the four mounts 82 mounted to one of the four arms 94 of the tail piece. More specifically, an axially directed bolt 96 extending from the mount 82 may extend through a bore 98 in an arm 94 of the tail piece and be held to the tail piece by a nut 102. With this attachment arrangement, it will be apparent that the mount 82 is free to rotate about the axis of the bolt 96. Further, it will be apparent that the mount 82 and resilient tail piece 64 together resiliently mount the tendon. The pulley frame 86 may have a central bore 104 which captures an axially directed, bolt 106 extending from the nose piece 62 so that the pulley frame 86 is free to rotate about the axis of the bolt 106.

Figure 8:
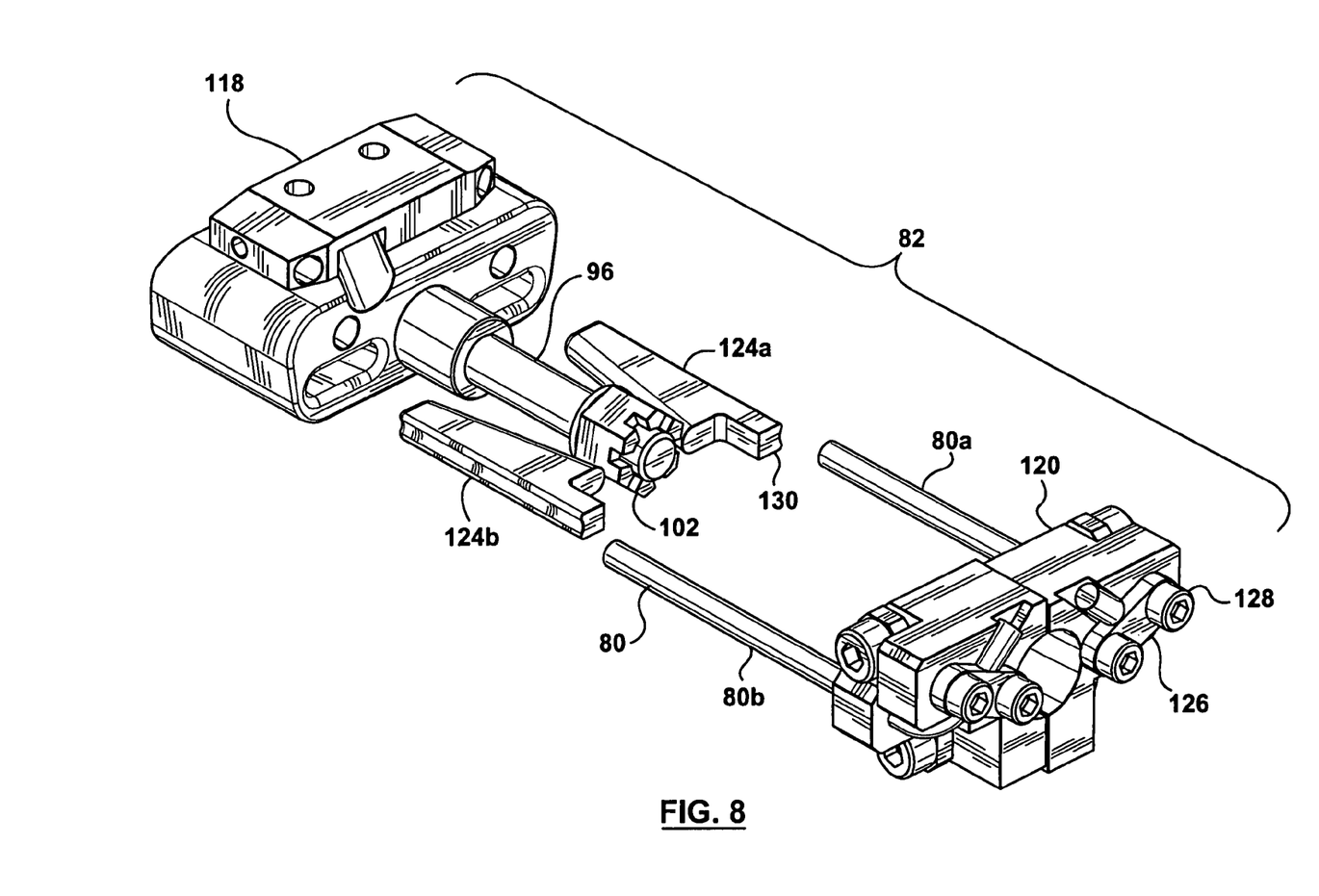
FIG. 8 is an exploded view of a portion of FIG. 7, and FIGS. 9a and 9b are schematic illustrations of a portion of the tool of FIG. 1 in operation.

With reference to FIG. 8, the mount 82 has a first member 118 and a second member 120. The bolt 96 is fixed to the first member 118. A pair of oval bores 122 extend through the first member for receiving tendon 80 and wedges 124a, 124b. The ends of the tendon 80 are secured to the second member by crimping these ends between plates 126 of the second member 120 by screws 128. With the tendon ends secured to the second member and the bolt 96 fastened to the tail piece 64 (FIG. 6), the first member 118, and the back end 130 of the wedges 124a, 124b abut the second member 120. The wedges act to reduce stress on the tendon 80 if its two arms 80a, 80b have been drawn closer together forwardly of the mount 82.

It should be apparent that the mounting arrangement for each skid allows the blocks of the skid a limited degree of radial and lateral freedom.

For any one skid (40a, 40b, 40c, 40d), the poles 52 are all at one side of the skid and are of the same polarity. Thus, the poles 54 are all at the opposite side of the skid. For example, poles 52 at one side of a given skid may be all north poles and poles 54 at the other side of that skid may be all south poles. In consequence, the flux lines generated by a given skid generally mimic the flux lines that would result if the magnets 50 in the blocks of a skid were replaced with a single spirally configured magnet. Further, it will be apparent that the pig 20 creates a magnetic field with transversely directed flux lines. The head and tail end conditioning blocks 39, 41 of a skid, which each have a magnet but no flux sensors, help ensure the magnetic field at the sensors of the head and tail end sensing blocks 42h, 42t are exposed to a uniform magnetic field.

As long as an even number of skids are used for unit 28, the skids may be made such that like poles of circumferentially adjacent skids are adjacent one another. (Thus, if the left hand side of a first skid is the north pole side, a second skid which is adjacent to the left hand side of the first skid with have its right hand side as its north pole side.) In consequence, the skids will repel each other, which will assist in keeping them equally angularly spaced. This also improves magnetic efficiency as the flux lines from the magnets of one skid are forced to stay in their own magnetic circuit and will not loop over to the magnets of an adjacent skid.

The magnets of the skids will impart an unwinding torque on the unit 28 which is resisted by the articulated dowell 60.

In operation, with the pig progressing along a pipeline, the magnetic field produced by the magnets 50 magnetically attracts the blocks of each skid into contact with the wall of the pipe. In this regard, the "give" provided by the tendon mounting of the blocks of the skid permit the blocks to move radially outwardly into contact with the pipe wall.

If the pig is progressing along a straight section of pipeline and encounters a restriction in the pipe, such as a dent, blocks hitting the dent may be deflected radially inwardly. This radial deflection is permitted by virtue of the tendon support for the blocks and also the flexible nature of the tail piece 64 and radial freedom provided by the length of the arms 80a, 80b of the tendon 80 between the leading edge of the head block 39 of each skid and the pulley frame 86. The strengthened and bevelled dome 43 of the head block 39 facilitates deflection of the blocks of a skid past a restriction without damage to the blocks. This is for the reason that the strengthened dome takes the full force of the deflection to deflect the head block 39 inwardly. When the head block 39 deflects, it pulls the next block 42h inwardly as well thereby reducing the force imparted to block 42h when it hits the restriction. This force lessening effect is repeated as subsequent blocks 42 hit the restriction and draw inwardly blocks that follow them.

Figure 9A:
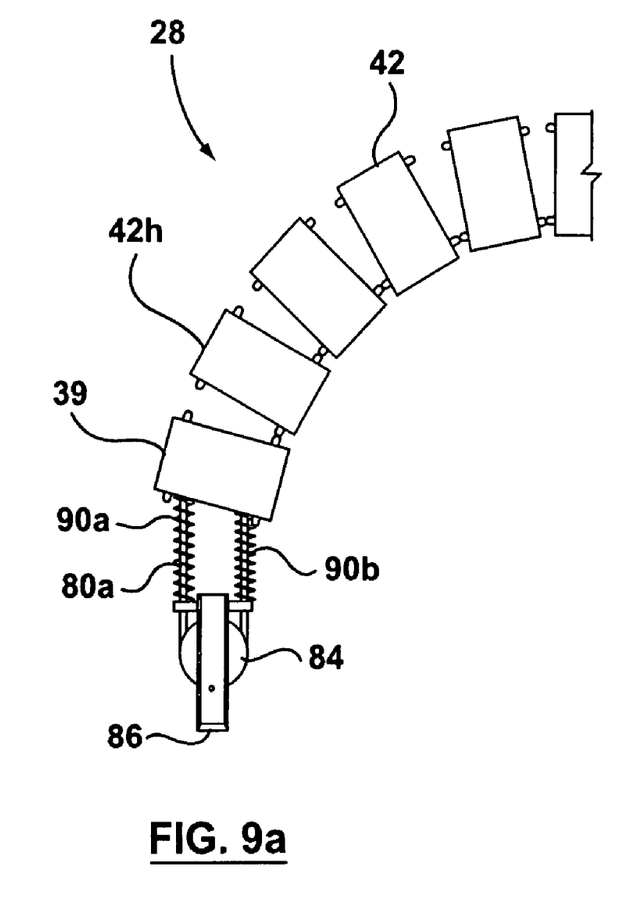
Figure 9B:
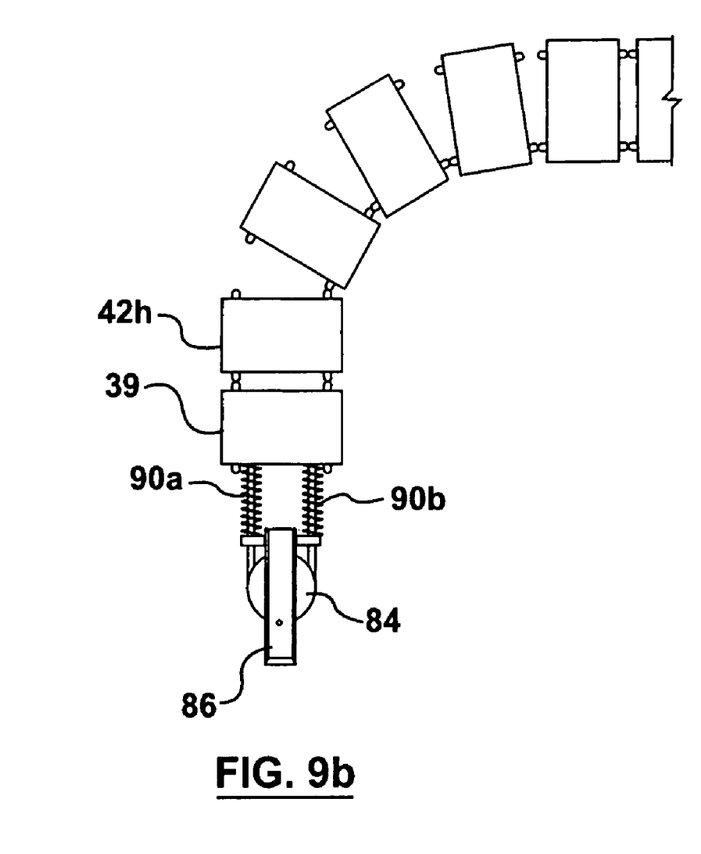

FIGS. 9a and 9b schematically show one skid of unit 28 (wherein, for simplicity of illustration, the spiral winding of he skid is not shown.) Turning to these figures, if the pig 20 reaches a bend in the pipeline, the side of each block 42 toward the outside of the bend within the bending section will separate from the outside side of its immediate neighbours. This action is allowed by the compression springs 90a, 90b. More specifically, when the unit 28 enters a curved section of pipe, pulley 84 will allow arm 80a of the tendon to increase in length compared with arm 80b and spring 90a with allow the outer side of each block to move away from its neighbouring blocks. Further, where the springs have cleared the curve, as shown in FIG. 9b, they will be equally compressed, but will be more compressed than they would be when the pig is travelling though an unrestricted linear section of the pipeline.

The articulations of the central dowel 60 also permit the unit 28 to travel through curves in the pipeline.

The maximum pipe curvature through which the pig may pass depends upon a number of variables, such as the length of the springs 90a, 90b between the head block 39 and the pulley frame 86 when the unit 28 is linearly disposed.

While the pig is travelling through the pipeline, the magnetic field sensors pass flux data to the electronic unit for storage. When the pig exits the pipeline, this data may be uploaded for analysis. Because the flux data is generated from spirally arranged skids, it will be apparent that this data will allow for a determination of both axially directed and non-axial directed flaws in the pipeline.

Although in the illustrated embodiment there are four equally circumferentially spaced skids, another number of equally circumferentially spaced skids may be used. For example, six, eight, ten, or twelve, equally circumferentially spaced skids could be employed. With six skids, each skid may have a head end sensing block displaced circumferentially from a tail end sensing block by about 60°. While two skids may also be possible for a unit 28, the head end sensing block may be displaced circumferentially from the tail end sensing block by about 180°. This would present an increased challenge to providing a skid with enough radial and lateral freedom to negotiate curves in a pipeline. While the illustrated embodiment has twelve sensing blocks, equally a greater or lesser number of sensing blocks may be employed.

While the invention has been described in the context of magnets and magnetic flux sensors, the invention also has application to blocks 42 having ultrasound generators and ultrasound sensors.

Springs 90a, 90b could be replaced by any other suitable mechanism to urge the blocks 42 together. For example, a cylindrical tube fabricated of a resilient material may surround each arm 80a, 80b of the tendon 80.

Pulley 84 could be replaced with, for example, a fixed rounded surface that permits the tendon to slide along the surface.

Other modifications will be apparent to those skilled in the art and, therefore, the invention is defined in the claims.

What is claimed is:

1. A pipeline inspection tool, comprising:
    a spirally arranged series of blocks extending between a pair of mounts, each block comprising a magnet and at least one magnetic flux sensor;
    a supporting tendon mounted to said mounts and extending through an opening in each block;
    a coil spring surrounding said tendon between one of said mounts and said series of blocks for compressing said blocks together.

2. The tool of claim 1 further comprising an axially extending support terminating in said mounts.

3. The tool of claim 2 wherein said support is arranged so as to permit bending of said series of blocks but resist torsion of said series of blocks.

4. The tool of claim 3 wherein said support comprises a series of members, each member joined to an adjacent member by a pin orthogonally directed to a longitudinal axis of said support such that a pin at one end of a given member is orthogonal to a pin at an opposite end of said member.

5. A pipeline inspection tool, comprising:
    a spirally arranged series of blocks, each block comprising a magnet and at least one magnetic flux sensor;

an axially extending support terminating in mounts and wherein said series of blocks is mounted between said mounts of said support;

a supporting tendon extending through an opening in each block of said series of blocks and mounted to said mounts of said support;

wherein said opening in each block is a first opening, and wherein said tendon extends from a second one of said mounts, through each said first opening, around a tendon support of a first of said mounts, said tendon support allowing movement of said tendon, and back through a second opening in each said block to said second mount.

6. The tool of claim 5 further comprising a compression spring surrounding each arm of said tendon between said tendon support and said series of blocks.

7. The tool of claim 6 wherein said tendon support comprises a pulley.

8. The tool of claim 7 wherein said second one of said mounts is resilient.

9. The tool of claim 6 further comprising a head-end block having a first opening and a second opening receiving said tendon and a magnet but no magnetic flux sensor, said head-end block positioned between said compression spring surrounding each arm of said tendon and said series of blocks and a tail-end block having a first opening and a second opening receiving said tendon and a magnet but no magnetic flux sensor, said tail-end block positioned between said second mount and said series of blocks.

10. The tool of claim 1 wherein said magnet of said each block is arranged such that a like pole of each magnet is at one side of said series of blocks.

11. The tool of claim 10 wherein poles of said each magnet are longitudinally elongated and said longitudinally elongated poles are directed along an axis of said tool.

12. The tool of claim 11 wherein said at least one magnetic flux sensor of said each block is between said poles of said magnet of said each block.

13. The tool of claim 10 wherein said series of blocks comprises one of a plurality of series of blocks disposed side-by-side about a circumference of said tool, each block of each of said plurality of series of blocks comprising a magnet and at least one magnetic flux sensor and wherein, for a given series of blocks, said magnet of each block of said given series of blocks is arranged such that a like pole of each magnet is at one side of said given series of blocks.

14. The tool of claim 13 wherein there is an even number of said plurality of series of blocks and said plurality of series of blocks are equally angularly spaced about a circumference of said tool.

15. The tool of claim 10 wherein a block at one end of said spirally arranged series of blocks is angularly displaced from a block at an opposite end of said spirally arranged series of blocks by an angle equaling about a quotient of 360° over the number of series of blocks.

16. The tool of claim 13 wherein a given pole of each block of said given series of blocks is adjacent a like pole of a circumferentially adjacent series of blocks such that said plurality of series of blocks repel one another.

17. A pipeline inspection tool, comprising:

a serially arranged series of blocks, each block comprising an energy generator and at least one energy sensor;

an axially extending support terminating in mounts, said series of blocks being mounted between said mounts of said support;

a tendon extending from a second one of said mounts, through a first opening in said each block, around a tendon support of a first of said mounts, said tendon support allowing movement of said tendon, and back through a second opening in said each block to said second mount.

18. The tool of claim 17 further comprising a compression spring surrounding each arm of said tendon between said tendon support and said series of blocks.

19. The tool of claim 18 wherein said tendon support comprises a pulley.

* * * * *